United States Patent [19]
Moroz

[11] Patent Number: 4,882,270
[45] Date of Patent: Nov. 21, 1989

[54] MONOCLONAL ANTIBODIES TO PLACENTAL ISOFERRITIN FOR USE IN DETECTING ONCOFETAL FERRITIN ASSOCIATED WITH BREAST CANCER AND HODGKINS DISEASE

[76] Inventor: Chaya Moroz, 40 Yehuda Hanassi Street, Tel Aviv, Israel

[21] Appl. No.: 148,133

[22] Filed: Jan. 22, 1988

Related U.S. Application Data

[63] Continuation of Ser. No. 568,275, Jan. 4, 1984, abandoned, which is a continuation-in-part of Ser. No. 373,715, Apr. 30, 1982, abandoned.

[30] Foreign Application Priority Data

May 15, 1981 [IL] Israel .................................... 62879

[51] Int. Cl.$^4$ .................. G01N 33/53; G01N 33/577; C12N 5/00; C12P 21/00
[52] U.S. Cl. .......................................... 435/7; 435/4; 435/68; 435/172.2; 435/240.26; 435/240.27; 435/810; 436/548; 436/801; 436/808; 436/811; 436/813; 530/387; 530/388; 530/808; 530/809; 530/828; 530/838; 530/846; 530/850; 935/89; 935/90; 935/95; 935/99
[58] Field of Search ...................... 435/4, 7, 68, 172.2, 435/240.26, 240.27, 810, 948; 436/548, 801, 808, 811, 813; 530/808, 809, 387, 388, 828, 838, 846, 850; 935/89, 90, 95, 99, 100, 102, 103, 104, 106, 107, 108, 110

[56] References Cited

U.S. PATENT DOCUMENTS 4,235,960 11/1980 Sasse et al. .............................. 435/7

OTHER PUBLICATIONS

Muller, C, et al., Jour Immunol. 131, No. 2:877–881 (1983).
Koskimies, S., et al, Nature, 264:480–482 (1976).
Liesegang, B. et al., PNAS, 75, No. 8:3901–3905 (1978).
Radbruch, A., et al., PNAS, 77, No. 5:2909–2913 (1980).
McKearn, T., et al., Immunol Rev., 47:91–115 (1979).
Yarmush, M., et al, PNAS 77, No. 5:2899–2903 (1980).
Schlom, J., et al, PNAS 77, No. 11:6841–6845 (1980).
Steinitz, M., et al, Immunobiol, 156:41–47 (1979).
Steinitz, M., et al., Journ Immunol, 125, No. 1:194–196 (1980).
Steinitz, M., et al., Immunol Today, Feb. 1981, pp. 38–39.
Croce, C., et al., Nature 228:488–489 (1980).
Olsson, T., et al., PNAS, 77, No. 9:5429–5431 (1980).
Steinitz, M., et al, Nature 269:420–422 (1977).
Zurawski, V., et al., Science 199:1439–1441 (1978).
Fiebig, H., et al., Acta Biol Med. Germ., 38:1627–1637, (1979).
Moroz, Ch. et al, "Preparation and Characterization of Monoclonal Antibodies Specific to Placenta Ferritin", Clinica Chimica Acta., 148 (1985) 111–118.
Moroz, Ch. et al, "Ferritin-Bearing Lymphocytes in the Diagnosis of Breast Cancer", Cancer, vol. 54; No. 1, Jul. 1, 1984, pp. 84–89.
Andersson, J. et al, "Frequencies of Mitogen-Reactive B Cells in the Mouse", The Journal of Experimental Medicine, vol. 145, 1977, pp. 1520–1530.
Moroz, Ch. et al, "Ferritin-Bearing Lymphocytes and T-Cell Levels in Peripheral Blood of Patients with Breast Cancer", Cancer Immunol. Immunother., 3, 101–105 (1977).
Giler, Sh., et al., "Immunodiagnostic Test for the Early Detection of Carcinoma of the Breast", Surgery, vol. 149, No. 5, pp. 655–657, Nov. 1979.
Kohler, G. et al, "Continuous Cultures of Fused Cells Secreting Antibody of Predefined Specificity", Nature, vol. 256, pp. 495–497, Aug., 1975.
Marcus, Donald M. et al, "Isolation of Ferritin from Human Mammary and Pancreatic Carcinomas by Means of Antibody Immunoabsorbents", Arch. Biochem. & Biophys., 162, 493–501.
Drysdale, James W. et al, "Carcinofetal Human Isoferritins in Placenta and HeLa Cells", Cancer Research, 34, 3352–3354, (1974).
Marcus, Donald M. et al, "Serum Ferritin Levels in Patients with Breast Cancer", Clin. Research, 447A (1975).

Primary Examiner—Robert J. Warden
Assistant Examiner—Jack Spiegel
Attorney, Agent, or Firm—Pennie & Edmonds

[57] ABSTRACT

There are provided monoclonal antibodies which react with human oncofetal ferritin and which do not react with human spleen ferritin or with liver ferritin; there are also provided monoclonal antibodies which react both with human placenta oncofetal ferritin and with human adult spleen ferritin. There is provided a process for producing clones producing such antibodies and such clones, and an assay for the detection of human breast cancer based on the determination of oncofetal ferritin, which assay is based on such monoclonal antibodies.

35 Claims, No Drawings

MONOCLONAL ANTIBODIES TO PLACENTAL ISOFERRITIN FOR USE IN DETECTING ONCOFETAL FERRITIN ASSOCIATED WITH BREAST CANCER AND HODGKINS DISEASE

CROSS REFERENCE TO RELATED APPLICATIONS

The present application is a continuation of application Ser. No. 568,275, filed Jan. 4, 1984, now abandoned, which in turn was a continuation-in-part of application Ser. No. 373,715, filed Apr. 30, 1982, now abandoned.

The present invention relates to monoclonal antibodies which react with human embryonic ferritin derived from human placenta, which do not react with adult human spleen or liver ferritin; and to monoclonal antibodies which react with human placenta embryonic ferritin and which cross-react with human adult spleen ferritin.

The invention further relates to an assay for the detection of human breast cancer and/or Hodgkins disease which comprises selectively determining when human oncofetal ferritin is present in the body tissues and/or lymphocytes of patients.

According to a specific embodiment of the present invention the presence or absence of human oncofetal ferritin is determined by a cytotoxic assay.

According to a further specific embodiment of the present invention, the presence or absence of human oncofetal ferritin is determined by a radio-immunoassay.

The assays according to the present invention are based on the use of the specific monoclonal antibodies in accordance with the present invention, which can be used in any type of suitable assay for the determination of the presence or absence of oncofetal ferritin, the presence of which is indicative in human patients that a breast cancer of stage I or II is present, or that Hodgkins disease is present.

According to a preferred embodiment of the present invention, the presence of oncofetal type ferritin on the surface of lymphocytes in the circulation of patients is determined, the presence of such ferritin being indicative of breast cancer or of Hodgkins disease.

STATE OF PRIOR ART

Ferritin is the major iron storage protein in tissues, and small amounts (65–150 ng/ml) can be detected in plasma. The analysis of normal tissue ferritin by isoelectric focusing has revealed considerable heterogeneity. Marcus and Zimberg (*Arch. Biochem. Biophysic.* 162, 493, 1974) showed that ferritin isolated from breast tumor tissues contained acidic isoferritin, not found in adult liver ferritin, while Drysdale and Singer (*Cancer Res.* 44, 3352, 1974) demonstrated acidic isoferritin in Hela tumor cells and in placenta cells. They suggested the term "carcinofetal" isoferritin for such isoferritin. It is also known as oncofetal ferritin.

Marcus and Zimberg, (*Clin. Res.* 23, A 447, 1975) and Jacobs et al (*Br. J. Cancer* 34, 286, 1976) reported increased serum ferritin concentrations in patients with breast cancer, and suggested its assay as a possible indicator for detecting breast cancer. However, since any heterologous anti-ferritin serum cross-reacts with antigenic determinants associated with both adult and oncofetal ferritin, it cannot distinguish between the two isoferritins. Their results were therefore significant only in patients in whom the ferritin level was above normal range (>200 ng/ml). In a recent study, Moroz et al., *Cancer Immunol.* and *Immunotherapy* 3,101, (1977) have identified a subpopulation of lymphocytes bearing ferritin on their surface in breast cancer patients. The ferritin is of the oncofetal type and these ferritin positive lymphocytes appeared in early stages of breast cancer (stage I–II). They were not found in patients with benign breast disease, or in healthy people (Giller et al, *Surgery Gyn. Obst.* 149, 655, 1979).

The identification of ferritin bound to lymphocytes or its presence in tissue fluids is the basis of the assay for the early detection of breast cancer in human patients.

In recent years, a method was developed by which one hybridizes mouse myeloma cells with hyperimmunized mouse spleen cells, (Kohler and Milstein, *Nature,* 256: 495: 1975). Such a hybrid cell can produce a single antibody directed towards a single antigenic determinant. After cloning of such hydrid cell, a clone of hybrid cells is thus obtained, producing a single monoclonal antibody.

SUMMARY OF THE INVENTION

The present invention concerns the production of a monoclonal antibody directed towards a single antigenic determinant available only on the oncofetal ferritin, and not on adult ferritin. The use of such an oncofetal ferritin-specific monoclonal antibody renders the identification of such an isoferritin in adult life (in plasma or on lymphocytes) a more specific and sensitive tool for the detection of a malignant disease. The chances of detecting a benign disease known to be associated with elevation of serum adult type ferritin significantly decreased.

The present invention deals with the production of two mouse monoclonal antibodies, each specific for a different antigenic determinant on human placental ferritin.

(1) CM-OF-H9- directed towards an antigenic determinant specific for human oncofetal ferritin (deposit number I-256 in the Collection Nationale de Cultures de Microorganismes of the Institut Pasteur in Paris, France) and (2) CM-OF-3- directed towards a determinant mutual to human embryonic ferritin and adult spleen ferritin.

The present invention further relates to a sensitive assay for the early detection of breast cancer. The assay also detects the presence of Hodgkins disease. The test is based on the identification of oncofetal ferritin in the serum and in other body fluids, or bound to lymphocytes, for the early detection of breast cancer and for the detection of Hodgkin's disease.

The unique specificity of the monoclonal antibody CM-OF-H9 to epitopes specific to oncofetal type ferritin, differentiates between elevation of serum ferritin caused by malignancy and the normal ferritin or that associated with benign diseases (e.g., thalassaemia). CM-OF-3 can detect the elevation of ferritin in the two groups of diseases. A test with both antibodies differentiates between the malignant and non-malignant diseases.

METHODS

Preparation of oncofetal ferritin

Ferritin was prepared from human placenta by a modification of the method used by Beamish et al. (*J. Clin. Path.* 24, 581, 1971). Placental tissue (500 gr) was sliced and water added to a total volume of 2000 ml. After homogenization the tissue suspension was heated to 75° C. for 20 minutes. The supernatant, after cooling and centrifugation at 10,000 rpm for 15 minutes, was treated with acetic acid to bring the pH to 4.6. The precipitated protein was removed by centrifugation at 10,000 rpm for 15 minutes and a clear supernatant was adjusted to neutral pH with dilute NaOH. When the clear brown supernatant was ultracentrifuged at 100,000 g for 240 minutes the suspended ferritin collected in a small button at the bottom of the tube. The precipitate was redissolved in 0.9% saline and further purified by passage through a Sephadex G200 column.

The ferritin fraction from this column was passed through a DEAE cellulose anion exchange resin using Tris-HCl buffer at pH 7.5 and a 0.02–0.5M gradient. Three protein peaks were obtained, the most acidic peak pI=4.8 (No. III) was collected and used for analysis. Its purity was shown by isoelectric focusing and immunoelectrophoresis against anti-ferritin serum and antihuman whole serum. This was used for the immunization of mice, see below.

PREPARATION OF HYBRIDOMAS

Myeloma Cells:

Myeloma cells used for hybridization-PB/NS1/1-Ag4–1 were grown in RPMI-1640 with 20% Fetal Calf Serum (FCS).

Mice

Balb/c Females, 4–6 weeks old initially.

Immunization protocol 3 weekly immunizations, of 50 μg of acidic ferritin in complete Freund's adjuvant, hybridizing 3 days after the last injection of 10 μg ferritin. Hyperimmune mice were rested at least one month before last boosting.

CELL PREPARATION

Spleen Cells a. Spleens were removed from mice in RPMI-0;
b. Rinsed 2× in petri dish with RPMI-0;
c. Teased apart in RPMI-0 with 18 ga. needles;
d. Cell suspension transferred to a tube and large chunks of tissue settled out;
e. Single cell suspension removed to a new tube spun at 800 RPM (160 xg) 5 min; Red blood cells lysed with 0.83% NH$_4$Cl, pH 7.5;
f. Cells washed 3× with RPMI-0, resuspended in same;
g. Cells counted with Trypan Blue.

Myeloma cells a. Cells were removed from culture flasks with gentle pipetting into 50 ml Falcon/Corning tube;
b. Spun down at 900 RPM (200 xg) 5 minutes;
c. Washed 1× with RPMI-0, resuspended in same and counted with Trypan Blue.

Spleen Cell-Myeloma combination a. Spleen and myeloma cells were combined in a 10:1 ratio in a single 50 ml conical Falcon/Corning disposable centrifuge tube;
b. Cells were pelleted at 900 RPM (200 xg) for 5 minutes;
c. Medium was aspirated as completely as possible;

All solutions and media used from now on were at room temperature; tube with cell pellet was immersed in a bath at 37° C., and the following was added accompanied by gentle stirring 0.2 ml 33% PEG 1500 for 1 minute, centrifuged at 200 g for 5 minutes. Cells were resuspended and stirred gently for 1 minute followed by the addition of 5 ml RPMI-0 gentle stirring and addition of 5 ml RPMI-0 20% Fetal Calf Serum. Hybrid mixture looked like a poorly resuspended cell suspension at this point with many small clumps;

e. The mixture was pelleted at 200 xg 5 minutes;
f. Cells were resuspended in RPMI-HY-HATD (at 37° C.) at a concentration of $3 \times 10^6$/cc by squirting medium onto the cell pellet;
g. Hybrids were plated out in flat bottom 96 well plates by adding 2 drops of cell suspension from a 5 ml pipet or with multi-pipettor using cut off tips (about 65 microliters), containing 100–120 RPMI-HY-HATD (Approx. $2 \times 10^5$ cells);
h. Control wells containing NS-1 cells + RPMI-HY-HATD at $1 \times 10^6$/ml were set up;
i. Plates were cultured for 7 days;
j. On day 8 and twice a week therefrom half of the culture medium was removed by careful aspiration and fed with 80–100 microliters of RPMI-HY-HT medium;
k. Positive wells were screened for at 3 and 4 weeks after hybridization.

Media and Solutions

1. RPMI-0 (No FCS)
2. RPMI 1640-HY
   500 ml sterile distilled water
   55 ml 10×RPMI-1640
   6 ml 1.0N Sodium Hydroxide
   14 ml 7.5% Sodium Bicarbonate

| 6 ml Pen/strep<br>10 ml Glutamine<br>86.5 ml FCS | + | DMEN |
|---|---|---|

3. RPMI-HY-HATD-day 0→day 7
   For 100 ml of medium
   95 ml RPMI−1640+20% FCS
   1.0 ml Pyruvate (100×)
   2.0 ml 50×HAT
   2.0 ml 50×deoxycytidine
4. RPMI-HY-HT-day 8→day 14
   For 100 ml of medium
   97 ml RPMI-1640+20% FCS
   2.0 ml 50×HT
   1.0 ml Pyruvate (100×)
   For Hybrids from day 15/onwards use RPMI-1640+20% FCS and Puruvate, or maintain in RPMI-HY-HT.
5. PEG 33 and 25% w/v
   Must be odorless and white. For 100 ml autoclave relevant wt in grams in a glas bottle at 15 lbs for 10–15 minutes. When bottle is cool enough to hand hold (about 50° C.) add RPMI 1640-0 to make up to 100 ml, swirl to mix, store at RT.
6. HATD-Final concentrations of reagents
   H=Hypoxanthine $10^{-4}$M
   A=Aminopyterin $10^{-6}$M
   T=Thymidine $2 \times 10^{-5}$M
   D=Deoxycytidine $2 \times 10^{-6}$M
   HT Stock 100×−100 cc
   ThymidineM.Wt, 242.33-0.04846 g
   Hypoxanthine M.Wt 136.1-0.1361 g.
   Add H$_2$O up to 100 ml and warm to 60°–70° C. to dissolve. Readjust final volume with dd H$_2$O. Dilute to 50× and filter (0.2μ) sterilize. Make 2 ml aliquots, store at −20° C.
   A Stock 1000×−100 cc
   Aminopterin F.Wt 440.4-0.44 g Bring to 50 ml with dd $H_2O$, add 0.1N NaOH dropwise until aminopterin dissolves. Bring final volume to 100 ml with dd $H_2O$. Adjust volume to 100 ml filter (0.2μ) sterilize. Store at −20° C.

D Stock 100× −100 cc

Deoxycytidine M.Wt 227.2 0.00454 g

Dissolve in dd $H_2O$, adjust to 100 cc, dilute to 50× stock, sterile (0.2μ) Filter, store at −20° C.

HAT-50× −200 ml

Combine 100 ml 100×HT with 10 ml 1000×A+90 ml dd $H_2O$=50×HAT, Filter (0.2μ) sterilize make 2 ml aliquots and freeze at −20° C.

Screening and determination of the specificity of the monoclonal antibodies was performed by a hemaglutination test.

Embryonic placenta and adult spleen ferritin were coupled to Ox red blood cells Ox RBC by $CrCl_2$. 50 μl of increasing dilutions (starting at 1:10 of hybridoma culture medium supernatant were mixed with 10 μl of adult or embryonic ferritin Ox RBC and hemagglutination determined.

Supernatants of clones giving a hemaglutination titer of at least 1:1000 were selected.

A clone designated CM-OF-3 was selected.

The clone CM-OF-3 is specific for embryonic ferritin and it cross-reacts with both adult and embryonic ferritin.

The monoclonal antibody obtained, CM-OF-3 was used to block the cross-reactive determinants of fetal and adult ferritin, in order to produce a different monoclonal antibody, CM-OF-H9, which is directed to a specific fetal determinant.

The following immunization procedure was used:

A. Immunization and Fusion Protocol.

Embryonic ferritin isolated from human placenta, a protein of pI 4.8 (see p. 4 and 5) was reacted with monoclonal antibodies CM-OF-3 in the following ratio: embryonic ferritin (90 μg in PBS) was mixed with Ascites fluid from BALB/c mouse containing CM-OF-3 antiferritin monoclonal antibodies (10 mgr/ml).

The mixture was incubated for 30 min at 37° C. followed by overnight incubation at 4° C. The mixture was centrifuged at 10,000 G, the precipitate formed was discarded, and the supernatant was used for immunization. Each BALB/c mouse was immunized with the above supernatant mixed with complete Freund's adjuvant, injected intradermally once a week for 3 weeks. A booster immunization of one fifth of the above dose was injected intraperitoneally.

After 3 days from boost, mouse spleen was aseptically removed and fusion was performed by incubating $10^8$ spleen cells with $10^7$/P3-NSI/1-Ag4 myeloma cells as set out above in the hybridization procedure and the same subsequent procedures for positive clone identification was followed. Thus a clone designated as CM-OF-H9 was obtained. This clone was deposited in the Collection Nationale de Cultures de Microorganismes of the Institut Pasteur in Paris, France, as deposit number I-256.

B. Characterization of the Monoclonal Antibody Obtained.

Characteristics of the CM-OF-H9 monoclonal antibodies: The CM-OF-H9 monoclonal antibody belongs to the $IgG_1$ class; it does not form precipitates with ferritin, it binds rabbit complement. In the ascitic fluid obtained, the antibody content was about 7 mg per ml. One ml of ascitic fluid binds about 2 mg of embryonic ferritin and none of adult spleen or liver ferritin.

While the particular clone obtained by the procedure described above is of the $IgG_1$ class it will be understood that it is the $F(ab)_2$ fragments of the antibody which determines its antigen binding specificity, and thus its utility in accordance with the present invention. The Fc fragment of the immunoglobulin molecule determines the isotype or species of the immunoglobulin but is immaterial to the applicability of the antibody for the purposes of the present invention. If the procedure described above is repeated a number of times, it would be expected that other types of immunoglobulin, such as IgM or IgD, would be produced. Such are all encompassed within the present invention as the monoclonal antibody obtained will still specifically bind to epitopes of oncofetal type ferritin but will not bind to epitopes of adult spleen or liver ferritin.

Furthermore, the source of the cells used to obtain the hybridoma in accordance with this invention is not limited to mouse spleen and mouse myeloma cells. Spleen cells or other lymphocytes of any animal can be used as long as the animal has been immunized against the specific human ferritin described above. Even lymphocytes of human breast cancer or Hodgkins disease patients can be used to obtain the hybridoma. Similarly the source of the myeloma is not critical, as long as it is capable of hybridizing with immunized lymphocytes.

It should be understood that clones productive of the specific monoclonal antibody of the present invention can be produced by genetic engineering, by means of recombinant DNA techniques well known in the art. Such techniques would not involve undue experimentation in view of the present state of the art of recombinant DNA technology and particularly when the monoclonal antibodies and the hybridoma produced by the processes described above are used as starting materials.

| Reactivity of Monoclonal Antibody | | |
|---|---|---|
| Source of human ferritin | CM-OF-H9 | CM-OF-3 |
| 1. Adult spleen from thalassaemia | − | + |
| 2. Normal serum | − | + |
| 3. Breast cancer (PBL)* | + | + |
| 4. Breast cancer (serum) | + | + |
| 5. Hodgkin's Disease (spleen) | + | + |
| 6. Benign breast disease (PBL)* | − | − |
| 7. Benign breast disease-serum | − | + |

*PBL: Peripheral blood lymphocytes

The two antibodies make possible a rapid and convenient detection of malignancies of the breast and of Hodgkin's disease, and a differentiation of these from thalassaemia, which results in an increase of ferritin.

PRINCIPLES OF SEROLOGICAL TEST PROCEDURES

Determination of Lymphocyte Bound Ferritin (LBF)

The presence of lymphocyte bound ferritin is indicative of the presence of breast cancer in human patients.

The determination of such ferritin is effected as follows:

a. Lymphocytes are isolated from peripheral blood;

b. Lymphocyte bound ferritin is determined by a conventional type of assay based on the use of the novel specific monoclonal antibodies, specific towards ferritin derived from human placenta.

According to a preferred embodiment the test is carried out as follows:

a. Lymphocytes are isolated from peripheral blood by Ficoll-Hypaque gradient centrifugation;
b. The presence or absence of LBF is determined by any conventional type of assay, such as cytotoxic test or radioimmunoassay.

Such assay can also be carried out with serum or other body fluids.

TEST FOR THE EARLY DETECTION OF BREAST CANCER AND HODGKINS DISEASE

Collection and Preparation of Cells

1. Blood collection tubes, 15 ml containing heparin.
2. Conical centrifuge tubes, 25 ml.
3. Pasteur pipettes and bulbs.
4. Sodium phosphate buffered saline of pH 7.2
5. Ficoll-Hypaque density solution 1.077 gm/ml.

Procedures for Collection of Cells

1. Collect 15 ml blood into a heparin-containing blood collection tube, dilute 1:2 in PBS pH 7.2
2. Underlay the cell suspension with 10 ml Ficoll-Hypaque density solution.
3. Centrifuge for 30 minutes at 300×g. room temperature.
4. Collect mononuclear cells from the medium: Ficoll-Hypaque interface with a Pasteur pipette and transfer to a new 15 ml tube.
5. Wash cells 3 times by suspension in 15 ml wash medium and centrifugation at 300×g for 10 minutes, at 4° C.
6. Resuspend in wash medium and determine cell number.

Radioimmunoassay (RIA)

Required Supplementary Material:
1. Minisorp test tubes 100×15 mm.
2. RPMI 1640
3. Bovine serum albumin (BSA) 5% in PBS of pH 7.2; containing 0.025% sodium azide
4. Normal rabbit serum (NRS)
5. CMH-9 monoclonal antibodies
6. Blanc Ascites fluid
7. 125 I anti-mouse IgG.

Radio-Immuno Assay—1

Peripheral blood mononuclear cells are isolated by Ficoll-Hypaque gradient centrifugation. Test is performed in triplicate. A Blank B Test.

1. Dispense $2\times10^6$ to $3\times10^6$ cells into each of six test tubes, pellet cells by centrifugation at 300 g for 10 min.
2. Add NRS 20 μl diluted 1:10 in PBS, incubate 60 min. at 4° C.
3. Add 30 μl of ascites fluids (dilution $10^{-5}$ in 5% BSA) to each of 3 tubes.
   A. Control ascites fluid containing an $IgG_1$ non-specific monoclonal antibody, non-reactive with oncofetal ferritin
   B. CMH-9 monoclonal antibodies mix well and incubate at room temperature during 2 hours.
4. Wash cells twice with 10 ml RPMI-1640 by centrifugation at 300 g for 10 min. at 4° C.
5. Add 0.1 μCi of $I^{125}$ rabbit anti-mouse IgG ($^{125}$I Rabbit IgG IμCi/μg) incubate 60 min. at 4° C. wash twice with cold RPMI-1640 as in 4, count radioactivity. Positive test Cpm A- CpmB<500.

Radio Immuno Assay—2

After Stage 1, RIA-1, the test procedure is continued as follows: CMH-9 F(ab)$_2$ is obtained by peptic digestion of CMH-9 IgG according to Utsumi and Karush (Biochem: 1965 4, 1766) and from the non-specific $IgG_1$ (see control of RIA-1). The F(ab)$_2$ fragments thus obtained are used as follows:

Tube A: Control F(ab)$_2$ in 5% BSA in PBS of pH 7.2; and 0.025% sodium azide.

Tube B: CMH-9 F(ab)$_2$ in 5% BSA in PBS of pH 7.2, and 0.025% sodium azide. Incubate during 60 minutes at room temperature, wash once with 2 ml of 1% BSA in pH 7.2 PBS; add $^{125}$I-labelled ligand to test tubes A and B (giving about $10^5$ cpm); either $^{125}$I-labelled oncofetal ferritin or a complex of $^{125}$I-polyclonal anti-oncofetal ferritin with oncofetal ferritin. The complex is pre-formed at antigen/antibody molar ratios of 1:1 or up to 1:2, pre-incubated with each other at room temperature for 1 hour. Incubate the labelled ligand together with cells for 1 hour at room temperature, wash twice with 1% BSA in pH 7.2 PBS to remove unbound labelled ligand and count. If B exceeds A the test is positive.

Cytotoxic Assay

Test is performed in duplicates.
A. Control B. Test.

1. Suspend PBL at a density of $5\times10^6$ cells/ml in RPMI-1640
2. Place 150 μl of PBL into each of 4 12×75 mm test tubes Add Ascites fluid (30 μl dilution $10^{-4}$) A. Control Ascites fluid (2 tubes). B. CMH-9 (2 tubes). Incubate 45 min. at 4° C.
3. Add rabbit complement (100 μl diluted 1:5 in PBS) and incubate 60 min. at 37° C. with slow agitation.
4. Count viable cells with Trypan blue.

Positive Test: =

$$\frac{\text{No. viable cells in } A - \text{No. viable cells in } B}{\text{No. of viable cells in } A} \times 100 \rightarrow 4\%$$

CYTOTOXICITY TEST KIT:
1. Monoclonal antibodies CMH-9
2. Monoclonal antibodies, non-specific
3. Rabbit complement
4. Conventional adjuvants in standardized solution.

RIA TEST KIT:
1. F(ab)$_2$ of CMH-9
2. F(ab)$_2$ of non-specific monoclonal
3. $^{125}$I-labelled ligand RIA-1 TEST KIT:
1. Monoclonal antibodies CMH-9
2. Monoclonal antibodies, non-specific
3. $^{125}$I-antimouse $IgG_1$
4. Adjuvants and standardized solutions

I claim:

1. Monoclonal antibodies which specifically bind to epitopes of human oncofetal ferritin antigens and which do not bind to epitopes of human spleen ferritin antigens or to epitopes of human liver ferritin antigens.

2. Monoclonal antibodies in accordance with claim 1, wherein said antibodies are of type IgG.

3. Monoclonal antibodies in accordance with claim 1, wherein said antibodies are murine antibodies.

4. F(ab)$_2$ fragments of monoclonal antibodies in accordance with claim 1.

5. Murine, IgG, monoclonal antibodies which specifically bind to epitopes of human oncofetal ferritin antigens and which do not bind to epitopes of human spleen ferritin antigens or to epitopes of human liver ferritin antigens.

6. The F(ab)$_2$ fragments of murine monoclonal antibodies which specifically bind to epitopes of human embryonal ferritin antigens and which do not bind to epitopes of human spleen ferritin antigens or to epitopes of human liver ferritin antigens.

7. Clone CM-OF-H-9 (I-256) producing monoclonal antibodies capable of binding with human embryonal ferritin antigens but incapable of binding with human spleen ferritin antigens or with human liver ferritin antigens.

8. Monoclonal antibodies which specifically bind to epitopes of human oncofetal ferritin antigens and which do not bind to epitopes of human spleen ferritin antigens or to epitopes of human liver ferritin antigens, produced by clone CM-OF-H-9 (I-256).

9. A kit for carrying out a cytotoxicity assay for the detection of breast cancer or Hodgins disease in humans comprising monoclonal antibodies in accordance with claim 1, monoclonal antibodies incapable of binding with oncofetal ferritin antigens and rabbit complement.

10. A kit for carrying out a radio-immuno assay for the detection of breast cancer or Hodgkins disease in humans, comprising F(ab)$_2$ of monoclonal antibodies in accordance with claim 4, F(ab)$_2$ of monoclonal antibodies incapable of binding with oncofetal ferritin antigens and $^{125}$I labelled oncofetal ferritin ligand.

11. A test kit for carrying out a radioimmunoassay for detection of breast cancer or Hodgkins disease in humans, comprising monoclonal antibodies in accordance with claim 1, monoclonal antibodies incapable of binding with oncofetal ferritin antigen, and $^{125}$I-anti immunoglobulin capable of binding to the monoclonal antibody of claim 1.

12. A kit for carrying out a cytotoxicity assay for the detection of breast cancer or Hodgkins disease in humans, comprising monoclonal antibodies in accordance with claim 5, monoclonal antibodies incapable of binding with oncofetal ferritin antigens and rabbit complement.

13. A kit for carrying out a radio-immunoassay for the detection of breast cancer or Hodgkins disease in humans, comprising F(ab)$_2$ of monoclonal antibodies in accordance with claim 5, F(ab)$_2$ of monoclonal antibodies incapable of binding with oncofetal ferritin antigens and $^{125}$I labelled oncofetal ferritin ligand.

14. A test kit for carrying out a radio-immunoassay for detection of breast cancer or Hodgkins disease in humans, comprising monoclonal antibodies in accordance with claim 5, monoclonal antibodies incapable of binding with oncofetal ferritin antigen and $^{125}$I-antimouse IgG$_1$.

15. A process for producing a clone which produces monoclonal antibodies which specifically bind to epitopes of human oncofetal ferritin antigens but do not bind to epitopes of human spleen ferritin antigens or to epitopes of human liver ferritin antigens, comprising:
(a) reacting embryonic ferritin derived from human placenta patient with monoclonal antibodies reactive with common binding sites on antigens of human oncofetal and human adult spleen ferritin to product ferritin having said common binding sites blocked by reaction with said monoclonal antibodies;
(b) immunizing an animal with the ferritin which is the reaction product of said reacting step (a);
(c) hybridizing sensitized lymphocytes of such animal with myeloma cells; and
(d) selecting a hybridoma clone producing monoclonal antibodies which specifically bind to epitopes of human embryonal ferritin antigens but do not bind to epitopes of human spleen ferritin antigens or to epitopes of human liver ferritin antigens.

16. A process according to claim 15, wherein the immunization is by a sequence of immunizations with said oncofetal ferritin in complete Freund's adjuvant.

17. A process according to claim 15, wherein the lymphocyte and myeloma cells are combined in a ratio of from 20:1 to 1:1.

18. A process according to claim 17, wherein said ratio is about 10:1.

19. A process in accordance with claim 15, wherein said animal immunized in said immunizing step is a murine animal.

20. A process according to claim 19, wherein the murine animal is a Balb/c female mouse.

21. A process for the production of monoclonal antibodies which bind to human embryonal ferritin antigens but do not bind to human spleen ferritin antigens or to human liver ferritin antigens, comprising:
cultivating a clone produced by the process of claim 15 and
injecting the clone into a recipient animal and removing ascitic fluid containing the monoclonal antibodies.

22. A clone producing monoclonal antibodies which bind to human embryonal ferritin antigens but do not bind to human spleen ferritin antigens or to human liver ferritin antigens, comprising the clone produced by the process of claim 15.

23. A process for producing a clone which produces monoclonal antibodies which specifically bind to epitopes of human oncofetal ferritin antigens but do not bind to epitopes of human spleen ferritin antigens or to epitopes of human liver ferritin antigens, comprising:
(a) reacting embryonic ferritin derived from human placenta with monoclonal antibodies reactive with common binding sites on antigens of human oncofetal and human adult spleen ferritin to produce ferritin having said common binding sites blocked by reaction with said monoclonal antibodies;
(b) immunizing a murine animal with the ferritin which is the reaction product of said reaction step (a);
(c) hybridizing sensitized spleen lymphocytes of such murine animal with myeloma cells; and
(d) selecting a hybridoma clone producing monoclonal antibodies which specifically bind to epitopes of human embryonal ferritin antigens but which do not bind to epitopes of human spleen ferritin antigens or to epitopes of human liver ferritin antigens.

24. A clone producing IgG monoclonal antibodies which bind to epitopes of human embryonal ferritin antigens but do not bind to epitopes of human spleen ferritin antigens or to epitopes of human liver ferritin antigens, consisting of the clone produced by the process of claim 23.

25. IgG monoclonal antibodies which specifically bind to epitopes of human oncofetal ferritin antigens and which do not bind to epitopes of human spleen ferritin antigens or to epitopes of human liver ferritin antigens, produced by a clone produced by the process of claim 23.

26. An assay process for the detection of the presence of oncofetal ferritin on or in lymphocytes, body tissues or blood serum of human patients, comprising:
   admixing said lymphocytes, body tissues or blood serum with monoclonal antibodies which specifically bind to epitopes of human oncofetal ferritin antigens and which do not bind to epitopes of human spleen ferritin antigens or to epitopes of human liver ferritin antigens; and
   determining the measure of binding of said antibodies with said lymphocytes, body tissues or blood serum.

27. An assay in accordance with claim 26 for the detection of the presence of oncofetal ferritin in the blood serum of human patients wherein said admixing step comprises admixing said blood serum with said monoclonal antibodies and said determining step comprises determining the measure of binding of said antibodies with said blood serum.

28. An assay in accordance with claim 26, wherein said monoclonal antibodies are murine, monoclonal antibodies.

29. An assay in accordance with claim 26, wherein said monoclonal antibodies are murine, IgG, monoclonal antibodies.

30. An assay process for the detection of breast cancer or of Hodgkins disease in humans by assaying for the presence of oncofetal type ferritin on lymphocytes or in blood serum derived from suspected breast cancer or Hodgkins disease patients, comprising:
   admixing said lymphocytes or blood serum with monoclonal antibodies which specifically bind to epitopes of human oncofetal ferritin antigens and which do not bind to epitopes of human spleen ferritin entigens or to epitopes of human liver ferritin antigens; and
   determining the measure of binding of said antibodies with said lymphocytes or said blood serum,
   wherein said measure of binding is indicative of the presence or absence of breast cancer or Hodgkins disease.

31. An assay process in accordance with claim 30, wherein said determining step is accomplished by means of cytotoxic assay.

32. An assay process for the detection of breast cancer or of Hodgkins disease in humans by assaying for the presence of oncofetal type ferritin on lymphocytes or in blood serum derived from suspected breast cancer or Hodgkins disease patients, comprising:
   admixing said lymphocytes or blood serum with monoclonal antibodies in accordance with claim 3; and
   determining the measure of binding of said antibodies with said lymphocytes or said blood serum,
   wherein said measure of binding is indicative of the presence or absence of breast cancer or Hodgkins disease.

33. An assay in accordance with claim 32 for the detection of the presence of oncofetal ferritin on the lymphocytes of human patients wherein said admixing step comprises admixing said lymphocytes with said monoclonal antibodies and said determining step comprises determining the measure of binding of said antibodies with said lymphocytes.

34. An assay process for the detection of breast cancer or of Hodgkins disease in humans by assaying for the presence of oncofetal type ferritin on lymphocytes or in blood serum derived from suspected breast cancer or Hodgkins disease patients, comprising:
   admixing said lymphocytes or blood serum with monoclonal antibodies in accordance with claim 2; and
   determining the measure of binding of said antibodies with said lymphocytes or said blood serum,
   wherein said measure of binding is indicative of the presence or absence of breast cancer or Hodgkins disease.

35. An assay process for the detection of breast cancer or of Hodgkins disease in humans by assaying for the presence of oncofetal type ferritin on lymphocytes or in blood serum derived from suspected breast cancer or Hodgkins disease patients, comprising:
   admixing said lymphocytes or blood serum with monoclonal antibodies in accordance with claim 5; and
   determining the measure of binding of said antibodies with said lymphocytes or said blood serum,
   wherein said measure of binding is indicative of the presence or absence of breast cancer or Hodgkins disease.

* * * * *